United States Patent [19]

Terwilliger

[11] Patent Number: 4,756,313

[45] Date of Patent: Jul. 12, 1988

[54] ULTRASONIC PROBE

[75] Inventor: Richard Terwilliger, San Ramon, Calif.

[73] Assignee: Advanced Diagnostic Medical Systems, Inc., Dublin, Calif.

[21] Appl. No.: 927,649

[22] Filed: Nov. 5, 1986

[51] Int. Cl.4 .......................... A61B 1/00; A61B 1/06; A61B 10/00

[52] U.S. Cl. ....................................... 128/660; 128/4; 128/6

[58] Field of Search ............... 128/660, 661, 662, 663, 128/4, 6, 24 A

[56] References Cited

U.S. PATENT DOCUMENTS

| | | | |
|---|---|---|---|
| 3,955,561 | 5/1976 | Eggleton | 128/660 |
| 4,375,818 | 3/1983 | Suwaki et al. | 128/4 |
| 4,550,608 | 11/1985 | Carnes et al. | 128/660 |

Primary Examiner—William E. Kamm
Assistant Examiner—George Manuel
Attorney, Agent, or Firm—Fliesler, Dubb, Meyer & Lovejoy

[57] ABSTRACT

An ultrasonic probe 10 includes an elongated housing 12 which contains a window 24 surrounding a ultrasonic transducer 32. The ultrasonic transducer 32 is mounted on a first platform 36. The first platform 36 is in turn mounted on a second platform 38. A motor 44 and linkage arrangement 48 is provided for pivoting the transducer 32. A thumb wheel 16 can rotatably position the transducer 32 as it pivots, allowing ultrasonic imaging of bodily tissue through three hundred and sixty degrees. Further, a position sensor 78 allows for accurate sensing of the position of the transducer 32 as the transducer 32 pivots and rotates.

23 Claims, 5 Drawing Sheets

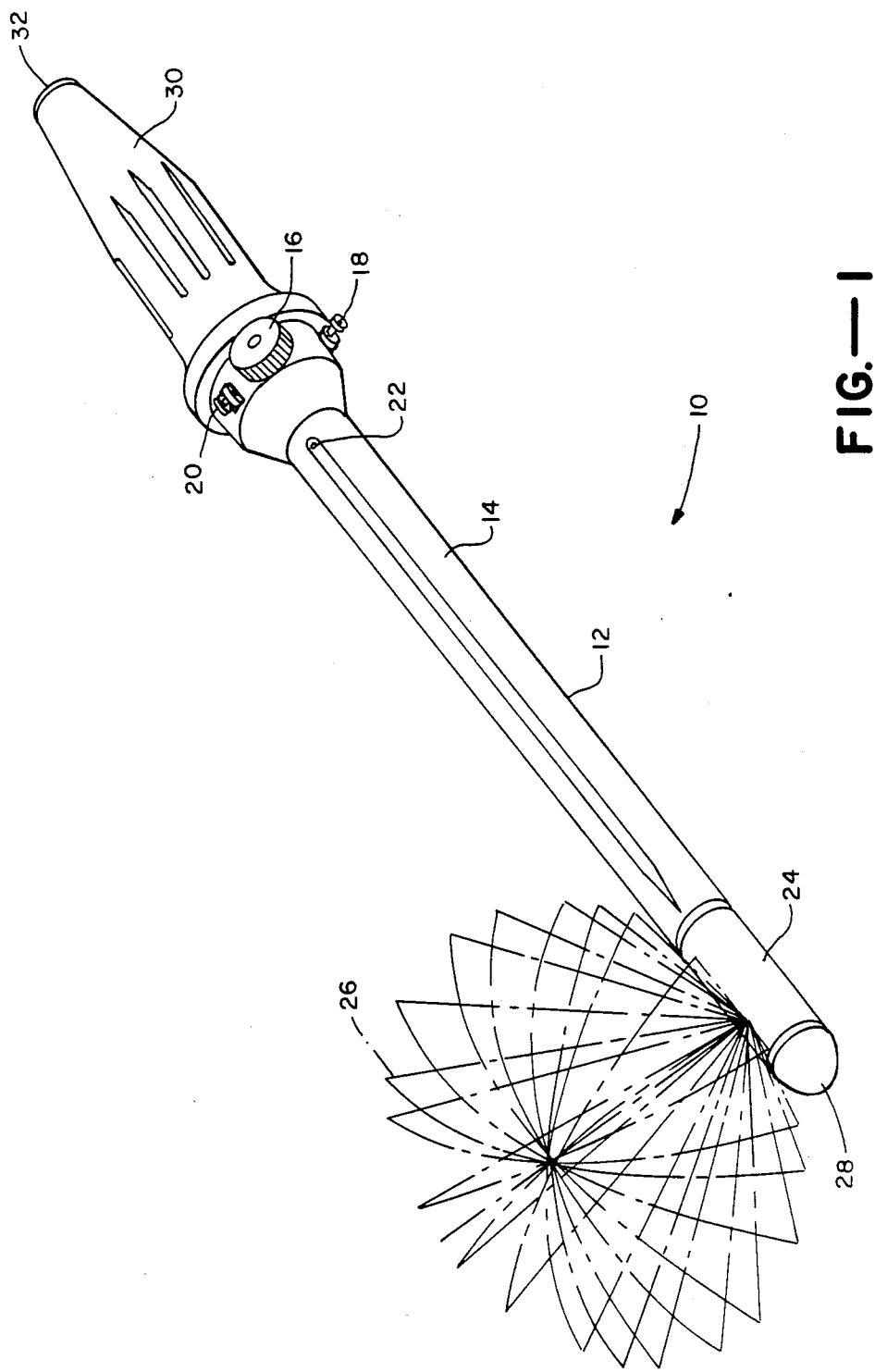

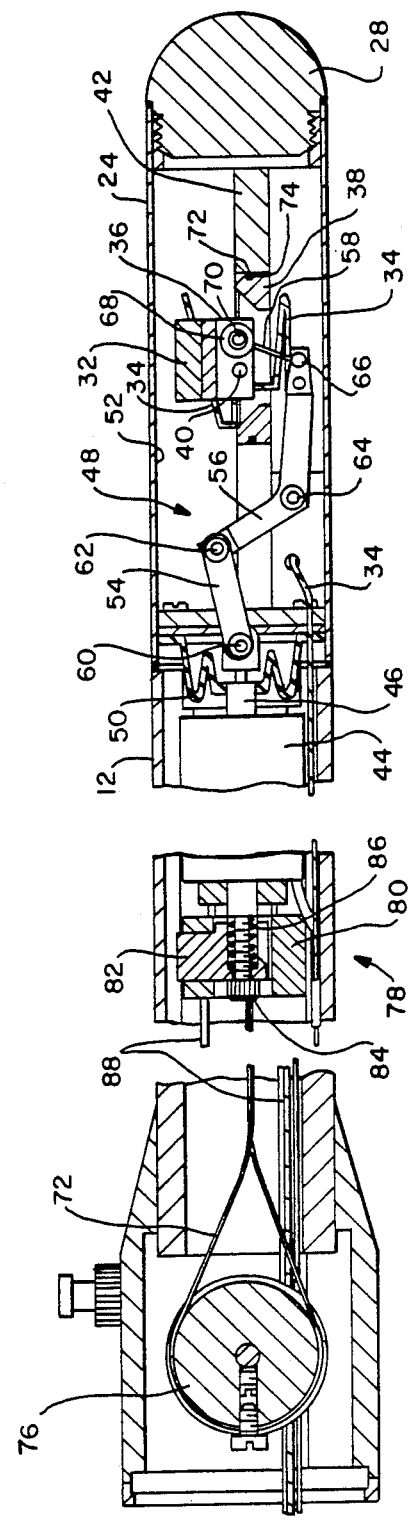
FIG.—2

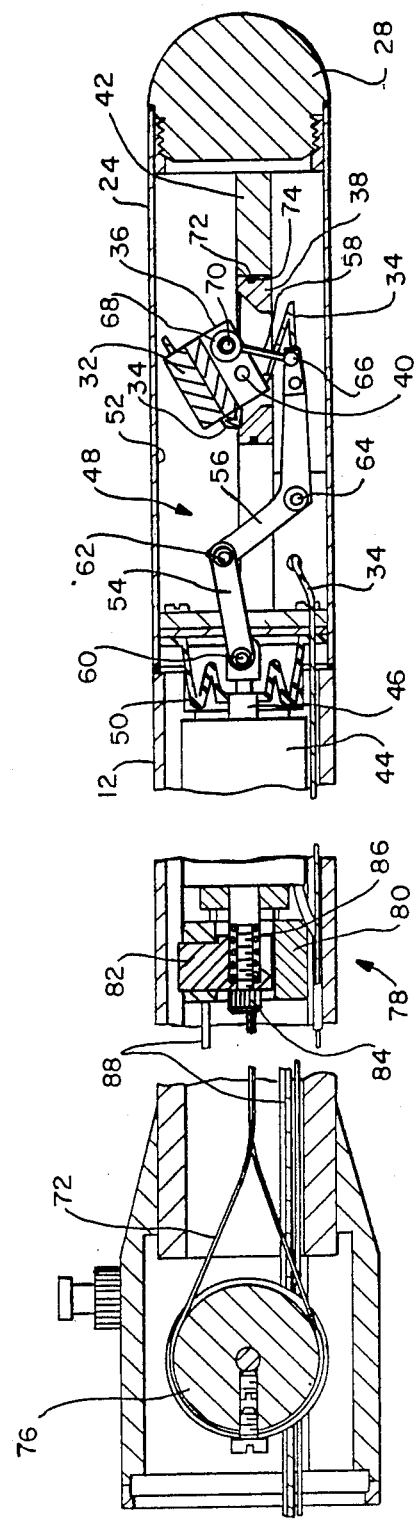
FIG.—2A

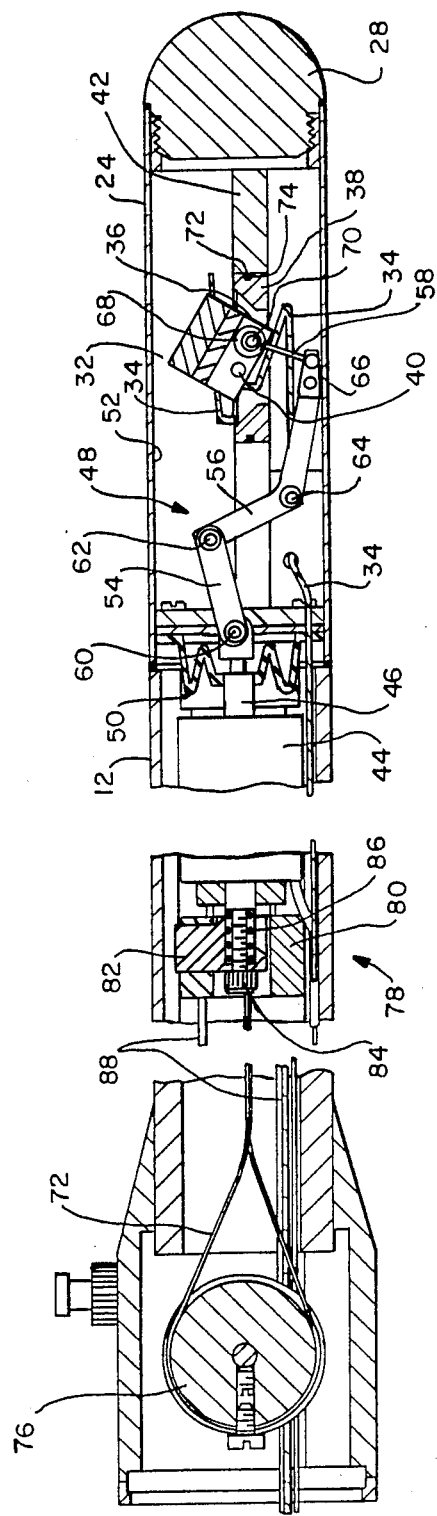
FIG.—2B

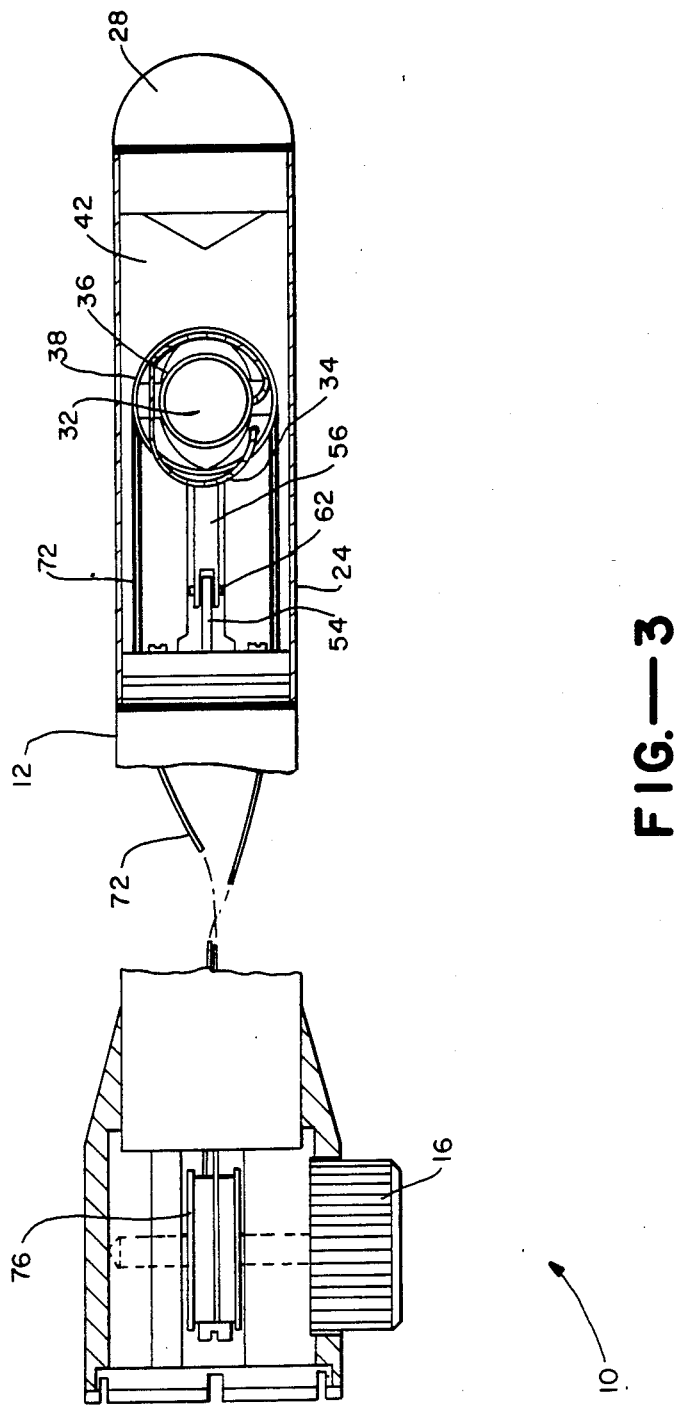
FIG.—3

ULTRASONIC PROBE

FIELD OF THE INVENTION

The present invention relates to ultrasonic probes and in particular to ultrasonic probes used for human intracavity examination.

BACKGROUND OF THE INVENTION

One of the several presently available noninvasive techniques for examining humans, as well as other animate and inanimate objects, includes the use of ultrasound to produce ultrasonic images of portions of the human bodily tissues which would otherwise be inaccessible except by surgical techniques. Ultrasound devices generally require the use of probes which can be applied either externally or internally with respect to the body in order to produce the appropriate image. Quite naturally, with probes that must be applied internally, it is important that the probe be made as small as possible so that the probes can be accommodated in the cavity, whether the cavity is that possessed by an infant or a fully grown adult.

An ultrasonic scanning probe is able to sample data so that an image can be made of a cross-sectional slice or plane through the body. Prior devices have been designed as elongated probes which have the capability of either taking an image representing a slice along the length of the probe or transverse to the length of the probe. The image is accomplished by causing an ultrasonic transducer to scan back and forth in the plane of the image. Prior devices have also been able to take an image by use of a fixed ultrasonic transducer which is located at the tip of the probe. Additionally, biplanar devices include both a scanning ultrasonic transducer for taking an image which is transverse to the probe and also a fixed ultrasonic transducer for taking an image along an axial or longitudinal plane.

The disadvantage of the first several probes which only allow for presenting an image in one plane, is that often times there is a requirement to present an image in another plane whether that plane be perpendicular to the first plane or at an oblique angle to the first plane. Thus, in order to accomplish this task, multiple probes are required. In the case of the biplanar probe, only two perpendicular views are presented, and no oblique views are possible. Further, it is to be understood that the two ultrasonic transducers in the biplanar probe are not positioned in the same location on the probe. Thus, in order to take images in two directions at the same position in the human body, the probe must be moved so that one and then the second sensor is properly positioned.

Accordingly, there is a need for a ultrasonic probe which is compact and which can allow for multiple imaging at any desired location.

SUMMARY OF THE INVENTION

The present invention is directed to overcoming the disadvantages of the prior art.

The present invention includes an ultrasonic probe capable of sending and receiving an ultrasonic signal. The probe includes an ultrasonic transducer and a mechanism for pivotally and rotationally mounting the ultrasonic transducer to a housing. The probe further includes a motor for pivoting the transducer and a device for operably connecting the motor to the mounting mechanism. The probe further includes a mechanism for rotating the transducer while the motor pivots the transducer.

The probe consequently provides for a transducer which can collect data to describe an image plane, which image plane can be represented on appropriate pictoral mechanisms such as, for example, a video monitor. As is evident from the above, the invention includes means for rotating the image plane so that images from one location on any desired plane can be obtained for the selected tissue under examination.

The present invention includes a linear motor with another transducer or sensor, for sensing the position of the motor. A linkage is provided between the linear motor and the another transducer. The position of the motor and, thus the ultrasonic transducer, is accurately measured by the position transducer. As the ultrasonic transducer is rotated, the relative relationship between the motor and the position of the ultrasonic transducer is not altered and, thus, the position transducer continues to give an accurate measurement of the position of the ultrasonic transducer no matter at what angle the ultrasonic transducer is set to obtain an image.

Accordingly, the present invention provides for a compact ultrasonic probe which can provide multiple imaging of human tissue with the probe located in one position relative to the body. In that position, an image representing a slice or plane through the tissue can be obtained at any or all desired angle. These images can be combined by an appropriate computer mechanism to provide a three dimensional image of the desired tissue.

Accordingly, it is an object of the present invention to provide a compact ultrasonic probe for intracavity examination.

It is yet another object of the present invention to provide a probe such that a single transducer located at one position on the probe can be used to take images representing slices or planes through the tissue at any desired angle without having to move the probe and without having to substitute another probe which has a transducer which allows an image to be taken in the next desired location.

Yet another object of the invention is to allow the transducer to change positions while the probe is inserted into the bodily cavity.

Yet a further object of the present invention is to provide for imaging through three hundred and sixty degrees at one location so that a truly three dimensional sonic image of the appropriate tissue can be reconstructed.

Yet a further object of the invention is to provide for a probe having an ultrasonic transducer which can be positioned at any desired angle and which includes another transducer for indicating the position of the ultrasonic transducer at whatever position the ultrasonic transducer is presently creating an image.

BRIEF DESCRIPTION OF THE FIGURES

FIG. 1 is a perspective view of the ultrasonic probe depicting the ability of the probe to take images at one location through any desired angle.

FIG. 2 is a side partial sectional view taken longitudinally along the probe of FIG. 1.

FIG. 2A is a side, partially sectioned view similar to FIG. 2 with the transducer tilted in one direction.

FIG. 2B is a side, partially sectioned view similar to FIG. 2 with the transducer tilted in a direction opposite to that depicted in FIG. 2A.

FIG. 3 is a plan partial sectional view which is substantially perpendicular to the view in FIG. 2 taken along a longitudinal axis.

DETAILED DESCRIPTION OF THE PREFERRED EMBODIMENT

With respect to the Figs., and in particular to FIG. 1, an ultrasonic probe is depicted and identified by the number 10. As can best be seen in FIG. 1, the probe 10 includes an elongated housing or body 12 which includes a cylindrical side surface 14. The probe 10 includes a thumb wheel 16 for rotationally positioning a ultrasonic transducer or sensor as describe below. The probe 10 further includes first and second exterior ports 18, 20 and two interior ports such as interior port 22 for the introduction of fluid as will be described below.

The ultrasonic probe 10 includes a window 24 formed as part of the elongated housing or body 12. As will be described below, an ultrasonic transducer is positioned in the probe immediately below the window 24 in order to send and receive ultrasonic signals as depicted in phantom at 26. The probe includes a distal end 28 and a handle 30. A multipin connector (not shown) can be inserted into the end 31 of handle 30 in order to connect the probe to the appropriate power supply and an appropriate computer device. The computer device provides an electrical signal to the ultrasonic transducer and receives from the ultrasonic transducer an appropriate response, and from the probe, a position signal. With the signal from the transducer and the position signal, the computer device can create an ultrasonic image of the tissue being sensed.

In FIGS. 2, 2A, 2B an ultrasonic transducer 32 is depicted. Transducer 32 is connected by way of lead 34 to the above indicated computer device. The ultrasonic transducer 32 is capable of alternatively sending and receiving ultrasonic signals and converting same to and from electrical pulses which are sent on lead 34. Transducer 32 is mounted on a first platform 36. First platform 36 is pivotally mounted on a second platform 38 and is allowed to pivot about a longitudinal pivot axis 40.

The second platform 38 is rotationally mounted in ultrasonic transducer housing 42 such that second platform 38 can rotate about an axis which is perpendicular to the plane of FIG. 3. Housing 42 is rigidly secured to the elongated body or house 12. In a preferred embodiment, the housing 12 is comprised of a suitably durable and cleanable plastic material which is used in medical applications and the window 24 is comprised of an appropriate clear plastic material.

Positioned midway through the elongated housing 12 in a preferred embodiment is linear motor 44. Also in a preferred embodiment the linear motor 44 oscillates at the rate of 20 Hz. Secured to the shaft 46 of the linear motor is a linkage arrangement 48 which operably connects the linear motor shaft 46 to the first platform 36 upon which the transducer 32 is mounted. Located immediately adjacent the linear motor 44 is a bellows seal 50 which is connected between the shaft 46 and the housing 12. The bellows seal 50, the cylindrical window 24 and the distal end 28 define a cavity 52 where the linkage arrangement 48, the first and second platform 36, 38 and the ultrasonic transducer 32 are located. In the preferred embodiment, this cavity 52 is filled with a fluid medium, preferably an oil, in order to enhance the transmission of ultrasonic signals to and from the transducer 32.

The linkage arrangement 48 includes a link arm 54, a crank arm 56 and a link rod 58. The link arm 54 is pivotally secured, at pivot point 60, to the shaft 46 of the linear motor 44. In a preferred embodiment, a jewelled pivot arrangement is provided at this location and also at the other pivot points in the linkage arrangement 48 in order to provide for a highly reliable and repeatable accurate mechanism for positioning the transducer 32 responsive to the position of the shaft 46 of the linear motor 44. The link arm 54 is pivotally secured to the crank arm 56 at pivot point 62. Crank arm 56 is pivotally secured at a midpoint 64 to the transducer housing 42. The distal end of crank arm 56 is secured by a ball and socket arrangement 66 to link rod 58. In turn, link rod 58 is secured to a ball and socket arrangement 68, which ball and socket arrangement 68 is it self pivotally mounted to first platform 36 along pivotally axis 70.

Second platform 38 is caused to rotate by a wire 72 that is secured in a outer circumvential groove 74 and which extends to a cable wheel 76 and is secured thereto. Cablewheel 76 is caused to turn by thumb wheel 16. It is to be understood that thumbwheel 16 could be replaced by an appropriate motor in order to motorize the rotation of the second platform 38. Thumb wheel 16 can cause second platform 38 to rotate through one hundred eighty degrees so that the transducer 32, as transducer 32 scans back and forth, can take an image through three hundred sixty degrees of rotation.

In order to sense the position of the shaft 46 of the linear motor 44 and thus the position of the transducer 32, a position sensor or transducer 78 is secured to the opposite end of the shaft 46 of the linear motor 44. The position sensor includes a toroidal magnet assembly 80 which in a preferred embodiment is made out of an iron composition and an encoder fin 82 which is secured to the shaft 46 by an appropriate screw 84 and compression spring 86 to ensure the accurate positioning of the fin 82 with respect to the shaft 46. In a preferred embodiment the fin 82 is comprised of aluminum. As the shaft 46 reciprocates, the fin 82 moves back and forth with respect to the toroidal assembly 80. As the encoder fin 82 moves relative to the toroid assembly 80, the inductance of the position sensor 78 changes and this change is sensed by lead 88 which communicates with the computer device (not shown). An appropriate sensing device, such as a potentiometer could be secured to the thumb wheel 16 in order, if desired, to provide the position of the thumb wheel to the computer device.

A sterile sheathing (not shown), preferably a pliable rubber type material, can be secured over the housing 12 before the housing is positioned in the body cavity. The sheathing is secured between the interior port 22 and the exterior ports 18 and 20. Through the exterior ports fluid may be introduced between the sheathing and the housing 12 in order to increase the transfer of ultrasonic signals to and from the transducer 32.

Industrial Applicability

In a preferred embodiment, as previously indicated, the linear motor 44 causes the transducer 32 through the linkage arrangement 48 to pivot at about 20 Hz about pivotal axis 40. The pivoting can be maintained through a complete rotation of the transducer 32 as previously explained. The position sensor 78 can accurately sense the position of the transducer 32 as transducer 32 is pivoted. This position is proportionately related to the change in inductance of the position sensor 78. This proportionality does not change as the transducer 32 is rotated by the thumb wheel 16 and, thus the position of the transducer 32 can be ascertained accurately at all times.

Further, in a preferred embodiment, the transducer can give a resolution of between 200 and 400 lines per inch, and take a desired image which is approximately 1/40,000 of an inch thick through the appropriate tissue.

From the above it is evident that the present invention has the advantage of being able to accurately and repeatedly position an ultrasonic transducer. Multiple images can be taken so that a three dimensional representation of the tissue can be presented on a computer screen. Further, as can be seen from the above, the present invention is compact, having only one ultrasonic transducer which has all the freedom of movement required in order to be able to select the appropriate image or images required to properly inspect the tissue.

It is to be understood, that while reference is made to using the probe 10 with human tissue, that probe 10 can work equally well with other types of tissue and materials whether living or not which can be inspected with ultrasound.

Other objects and aspects of the invention can be ascertained by a review of the Figs. and the Claims appended hereto. It is to be appreciated by one of ordinary skill in the art that other variations on the above preferred embodiment can be accomplished and be within the spirit and scope of the Claims.

I claim:

1. A probe comprising:
   a probe housing;
   a transducer capable of at least one of sending and receiving a signal;
   means for pivotally mounting said transducer relative to said housing;
   means for rotationally mounting said pivotally mounting means to said housing;
   means for pivoting said transducer so that the signal of the transducer drescribes a signal plane as the transducer pivots;
   means linking said transducer pivoting means to said pivotally mounting means;
   and said pivotally mounting means while said transducer pivoting means pivots said transducer, such that said signal plane described by the pivoting transducer can be caused to rotate.

2. The probe of claim 1 wherein said transducer is an ultrasonic transducer.

3. The probe of claim 1:
   wherein said rotationally mounting means includes a transducer housing secured inside said probe housing, and a first platform rotatably mounting in said transducer housing; and
   wherein said pivotally mounting means includes a second platform pivotally mounted to said first platform; and
   wherein said transducer is secured to said second platform.

4. The probe of claim 3 wherein said linking means includes:
   a link arm pivotally secured to said transducer pivoting means;
   a crank arm pivotally secured to said link arm and pivotally secured to said transducer housing;
   a shaft means for operably connecting said crank arm to said second platform;
   means for securing said shaft means to said crank arm such that said shaft can move along any combination of three perpendicular directions;
   means for securing said shaft means to said second platform, at a location other than where said second platform is pivotally secured to said first platform, such that said shaft can move along any combination of three perpendicular directions.

5. The probe of claim 4 including means for accurately sensing the pivotal position of the transducer as the transducer is pivoted and rotated.

6. The probe of claim 5 wherein:
   said transducer pivoting means includes a shaft; and
   said probe further including
   means for securing said link arm to said shaft; and
   means for securing said sensing means to said shaft.

7. The probe of claim 3 wherein said probe housing includes a handle located distally from said transducer and wherein said rotating means includes a pully mounted in said handle and a cable secured to said first platform and to said pulley for rotating said first platform relative to said transducer housing responsive to the rotating of said pulley.

8. The probe of claim 1 wherein said transducer pivoting means includes a linear reciprocating motor.

9. The probe of claim 1 including a sensor means for sensing the position of said transducer pivoting means in order to determined the position of said transducer.

10. The probe of claim 1 wherein said sensor means includes a toroid magnet, a fin and means for securing the fin to the transducer pivoting means for positioning the fin relative to the toroid magnet.

11. The probe of claim 1 including means for accurately sensing the pivotal position of the transducer as the transducer is pivoted and rotated.

12. A probe comprising:
   a probe housing;
   a transducer capable of at least one of sending and receiving a signal;
   means for pivotally and rotationally mounting said transducer;
   means for pivoting said transducer;
   means for operably connecting said pivoting means to said mounting means for pivoting said transducer so that the signal of the transducer describes a signal plane as the transducer pivots;
   means for rotating said transducer while said pivoting means pivots said transducer; and
   means for operably connecting said rotating means to said mounting means, such that said signal plane described by the pivoting transducer can be caused to rotate.

13. The probe of claim 12 wherein said transducer is an ultrasonic transducer.

14. The probe of claim 12 wherein said pivotally and rotationally mounting means include:
   means for pivotally mounting said transducer relative to said housing; and
   means for rotationally mounting said pivotally mounting means to said housing; and wherein said transducer pivoting means includes
   motor means for pivoting said transducer,
   wherein said rotationally mounting means includes a transducer housing secured inside said probe housing, and a first platform rotatably mounted in said transducer housing; and wherein said pivotally mounting means includes a second platform pivotally mounted to said first platform; and wherein said transducer is secured to said second platform.

15. The probe of claim 14:

wherein said rotationally mounting means includes a transducer housing secured inside said probe housing, and a first platform rotatably mounted in said transducer housing; and wherein said pivotally mounting means includes a second platform pivotally mounted to said first platform; and wherein said transducer is secured to said second platform.

16. The probe of claim 15 wherein said means for operably connecting said pivoting means to said mounting means includes:

a link arm pivotally secured to said transducer pivoting means;

a crank arm pivotally secured to said link arm and pivotally secured to said transducer housing;

a shaft means for operably connecting said crank arm to said second platform;

means for securing said shaft means to said crank arm such that said shaft can move along any combination of three perpendicular directions;

means for securing said shaft means to said second platform, at a location other than where said second platform is pivotally secured to said first platform, such that said shaft can move along any combination of three perpendicular directions.

17. An elongate probe capable of at least one of sending and receiving a signal comprising:

an elongate housing having an elongate side surface and first and second ends;

a transducer capable of at least one of sending and receiving a signal;

means for pivotally mounting said transducer relative to said housing along said elongate side surface such that the signal can describe a signal plate that is substantially perpendicular to said elongate side surface;

means for rotationally mounting said pivotally mounting means;

means for pivoting said transducer so that the signal of the transducer describes said signal plane as the transducer pivots;

means linking said transducer pivoting means to said pivotally mounting means;

means for rotating said pivotally mounting means while said transducer pivoting means pivots said transducer, such that said transducer can rotate, and such that the signal plane described by the pivoting transducer can be caused to rotate.

18. The probe of claim 17:

wherein said rotationally mounting means includes a transducer housing secured inside said probe housing and a first plaform rotatably mounted in said transducer housing; and wherein said pivotally mounting means includes a second platform pivotally mounted to said first platform; and wherein said transducer is secured to said second platform.

19. The probe of claim 18 wherein said linking means includes:

a link arm pivotally secured to said transducer pivoting means;

a crank arm pivotally secured to said link arm and pivotally secured to said transducer housing;

a shaft means for operably connecting said crank arm to said second platform;

means for securing said shaft means to said crank arm such that said shaft can move along any combination of three perpendicular directions;

means for securing said shaft means to said second platform, at a location other than where said second platform is pivotally secured to said first platform, such that said shaft can move along any combination of three perpendicular directions.

20. The probe of claim 17 wherein said transducer is an ultrasonic transducer.

21. An elongate probe capable of at least one of sending and receiving a signal comprising:

an elongate housing having an elongate side surface;

a transducer capable of at least one of sending and receiving a signal;

means for mounting said transducer along said elongate side surface;

means for moving said transducer mounting means such that said signal transducer describes a signal plane;

means moving said transducer mounting means such that the signal plane rotates about an axis located in the signal about an axis located in the signal plane.

22. The probe of claim 21 wherein said means for rotating said signal plane includes means for rotating said signal plane through approximately 180°.

23. The probe of claim 21 wherein said transducer is an ultrasonic transducer.

* * * * *

UNITED STATES PATENT AND TRADEMARK OFFICE
CERTIFICATE OF CORRECTION

PATENT NO. : 4,756,313

DATED : July 12, 1988

INVENTOR(S) : Richard Terwilliger

It is certified that error appears in the above-identified patent and that said Letters Patent is hereby corrected as shown below:

Column 3, line 13, "as describe below" should be --as described below--

Column 4, line 16, "is it self pivotally" should be --is itself pivotally--

Claim 1

Column 5, line 41, "drescribes" should be --describes--

Column 5, line 45, The following should be added to the beginning of line 45: --means for rotating said rotationally mounting means--

Claim 3

Column 5, line 54, "mounting" should be --mounted--

Claim 9

Column 6, line 29, "to determined the" should be --to determine the--

Claim 14

Column 6, line 65 through Column 7, line 5 should be deleted. A period should be placed after the word "transducer" in line 64.

UNITED STATES PATENT AND TRADEMARK OFFICE
CERTIFICATE OF CORRECTION

PATENT NO. : 4,756,313

DATED : July 12, 1988

INVENTOR(S) : Richard Terwilliger

It is certified that error appears in the above-identified patent and that said Letters Patent is hereby corrected as shown below:

<u>Claim 17</u>

Column 7, line 43, "a signal plate" should be --signal plane--.

<u>Claim 21</u>

Column 8, line 44, the word --for-- should be inserted between the word "means" and the word "moving"

Column 8, line 46, the words "about an axis located in the signal" should be deleted.

Signed and Sealed this

Twenty-eighth Day of February, 1989

*Attest:*

DONALD J. QUIGG

*Attesting Officer*     *Commissioner of Patents and Trademarks*